United States Patent [19]

Weston

[11] 4,062,869

[45] Dec. 13, 1977

[54] PROCESS FOR PREPARATION OF TRYPTOPHOLS

[75] Inventor: George Oliver Weston, Havant, England

[73] Assignee: John Wyeth & Brother Limited, Maidenhead, England

[21] Appl. No.: 692,619

[22] Filed: June 3, 1976

[30] Foreign Application Priority Data

June 3, 1975 United Kingdom ............... 23884/75

[51] Int. Cl.$^2$ .......................................... C07D 209/12
[52] U.S. Cl. ............................................... 260/326.16
[58] Field of Search .................................... 260/326.16

[56] References Cited

U.S. PATENT DOCUMENTS

| 2,825,734 | 3/1958 | Speeter ................... 260/326.14 R X |
| 3,076,814 | 2/1963 | Speeter et al. .......... 260/326.14 R X |
| 3,352,856 | 11/1967 | Szmuszkovicz ...................... 260/240 |

*Primary Examiner*—Ethel G. Love
*Attorney, Agent, or Firm*—Arthur E. Wilfond

[57] ABSTRACT

A process for preparing tryptophol derivatives comprises reducing a 3-indolylglyoxylic acid ester or acid halide using an alkali metal borohydride in the presence of an alcohol or ether solvent. The tryptophol derivatives prepared are useful as intermediates to pharmacologically active compounds.

9 Claims, No Drawings

PROCESS FOR PREPARATION OF TRYPTOPHOLS

This invention relates to a process for the preparation of 1-unsubstituted-3-(2-hydroxyethyl)indole derivatives, such as tryptophol.

U.S. Pat. No. 3,076,814 describes the preparation of 3-(2-hydroxyethyl)indoles by reducing 3-indoleglyoxylic acids using lithium aluminium hydride. The patent also discloses the partial reduction of the 3-indoleglyoxylic acids using sodium borohydride to give 3-indoleglycolicacids; which compounds, it states, can be reduced further to the 3-(2-hydroxyethyl)indoles by lithium aluminium hydride.

It has now surprisingly been found that, in certain solvents, 1-unsubstituted-3-indoleglyoxylic acid esters and acid halides may be reduced with alkali metal borohydride reducing agents to give 1-unsubstituted 3-(2-hydroxyethyl)indole derivatives.

The ability to carry out the reduction to give tryptophols using borohydrides gives the process of this invention advantages over the known process using lithium aluminium hydride. For example alkali metal borohydrides are relatively safe reagents and reduction may be effected smoothly. Reductions using lithium aluminium hydride on the other hand are more hazardous. The present invention, therefore, provides a process which is suitable for large - scale preparations. The use of sodium borohydride is particularly advantageous as this reagent is less expensive than lithium aluminium hydride. Further advantages over the use of LiAlH$_4$ include the ability to have substituents present on the indole ring which are unaffected by the borohydride reducing conditions and which would be reduced by the more powerful LiAlH$_4$. Such groups include alkoxycarbonyl, carboxy and cyano substituents.

The 3-(2-hydroxyethyl)indoles prepared by the process of this invention in general are known compounds and are valuable chemical intermediates useful in the preparation of therapeutically active compounds. In particular the process of this invention provides a simple and convenient process for the preparation of "tryptophol", i.e. 3-(2-hydroxyethyl)indole.

In one aspect therefore this invention provides a process for preparing a 1-unsubstituted-3-(2-hydroxyethyl)indole which comprises reducing a 1-unsubstituted-3-indoleglyoxylic acid ester or acid halide with an alkali metal borohydride in the presence of an alcohol or ether solvent suitable for effecting the reduction.

In a preferred embodiment the present invention provides a process for preparing a tryptophol derivative of formula:

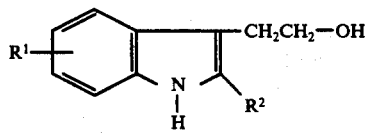

(I)

wherein R$^1$ represents hydrogen, halogen, lower alkoxy, lower aralkoxy, hydroxy or lower alkyl, and R$^2$ represents hydrogen, lower alkyl or aryl, which comprises reducing a compound of formula

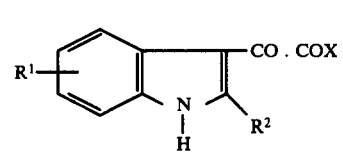

(II)

wherein R$^1$ and R$^2$ are as defined above and X represents halogen, e.g. chlorine or bromine, or the group OR wherein R represents alkyl, aryl or aralkyl, preferably lower alkyl or lower aralkyl; with an alkali metal borohydride.

The terms "lower alkyl" and "lower alkoxy" as used herein mean the radical contains from 1 to 6, preferably 1 to 4 carbon atoms and the terms "lower aralkyl" or "lower aralkoxy" mean the radical contains 7 to 12, preferably 7 to 9, carbon atoms e.g. benzyl, phenethyl.

By the term "aryl" is meant a carbocylic or heterocyclic radical having aromatic character, e.g. phenyl. Examples of R$^1$ are hydrogen, chlorine, methoxy, ethoxy, hydroxy, methyl, ethyl, n-propyl, isopropyl, n-butyl, isobutyl or benzyloxy. Preferably R$^1$ is a hydrogen atom. R$^2$ can be, for example, hydrogen, methyl, ethyl, n-propyl, isopropyl, n-butyl, isobutyl or substituted or unsubstituted phenyl and is preferably hydrogen or methyl.

Examples of the group R are phenyl; substituted phenyl, e.g. phenyl substituted by halogen (e.g. chlorine) lower alkyl (e.g. methyl) or lower alkoxy (e.g. methoxy); methyl; ethyl; n-propyl; isopropyl; n-butyl; benzyl phenethyl, or benzyl substituted by the same groups as for phenyl. Preferably R is lower alkyl or lower aralkyl. Most preferably R is methyl or benzyl.

A particularly preferred embodiment of the present invention provides a novel process for preparing tryptophol which comprises reducing a 3-indoleglyoxylic acid ester or acid halide of formula

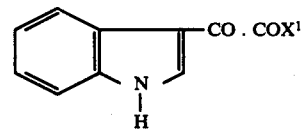

(III)

wherein X$^1$ represents halogen or —OR$^5$ wherein R$^5$ represents aryl, lower alkyl, or lower aralkyl, with an alkali metal borohydride. Preferably R$^5$ is methyl or benzyl.

The alkali metal borohydride reducing agents used in the novel process of this invention are well known in the literature and can be, for example, lithium, potassium or sodium borohydride. The preferred alkali metal borohydride is sodium borohydride; the use of such a reagent is particularly surprising since it does not normally reduce ester groups nor does it normally reduce carbonyl groups to methylene groups.

Auxiliary reagents used in reduction processes, e.g. halides such as boron trifluoride, may be employed with the alkali metal borohydride in the process of the invention.

The reduction may be conveniently carried out by mixing the 3-indoleglyoxylic acid ester or acid halide with the alkali metal borohydride in the presence of a suitable solvent and warming, the mixture gently, if necessary, to initiate reaction. Examples of suitable solvents are alkanols having 2 or more carbons, e.g. 2 to 6 carbons such as ethanol n-propanol, isopropanol and n-butanol; ether derivatives of glycol such as diglyme and dimethoxymethane; and dioxane. After any initial exothermic reaction is complete the reduction may then be brought to completion by heating or refluxing the mixture for a period of time sufficient to complete the reaction. Heating to high temperatures, e.g. between about 78° C and about 180° C, depending on the solvent may be used to complete the reaction. Preferred reaction temperatures are between about 80° C and about 120° C. Isopropanol is the preferred solvent. Preferably the borohydride is employed in a molar ratio of from 2 to 4 mols borohydride per mol of starting material; most preferably 2 to 3, e.g. about 2.2, mols borohydride per mol of starting material are used.

Many of the compounds of formula I prepared by the process of this invention are useful as starting materials for the preparation of therapeutically active compounds for example, as described in U.K. Patent Specification No. 1,375,836. The compounds of formula I may also be converted to the 2-(indol-3-yl) ethyl halides using hydroxyl/halogen exchange reagents, e.g. to the bromide using PBr$_3$; which compounds may then be used to prepare therapeutically active compounds as described in U.K. Patent Specification No. 1,218,570, corresponding to U.S. Pat. No. 3,527,761. By "a hydroxyl/halogen exchange reagent" is meant a reagent capable of displacing the hydroxyl group of an alcohol by a halogen atom. Typical examples are PBr$_3$, PCl$_3$, sulphonyl chloride, etc.

The 3-indoleglyoxylic acid ester or acid halide derivatives used as starting materials are known compounds or may be prepared by knwon procedures. For example an indole may be reacted with an oxalyl halide to give a 3-indoleglyoxylyl halide which may then be reacted with an alcohol, e.g. an alcohol of formula ROH wherein R is as defined above, preferably in the presence of a base to give the corresponding 3-indoleglyoxylic acid ester. Examples of alcohols of formula ROH are methanol, ethanol, butyl alcohol, benzyl alcohol, m-cresol and the like.

The following non-limiting Examples illustrate the novel process of this invention. Temperatures are in ° C.

EXAMPLE 1

3-(2-Hydroxyethyl)indole

A vigorously-stirred mixture of isopropanol (3 l), methyl 3- indolylglyoxylate (305 g) and sodium borohydride (125 g) was warmed to 40° – 50° and held at that temperature until the initial exothermic reaction was complete. The mixture was then heated to reflux for 4 hours, cooled and diluted with water (5 l). After acidification with hydrochloric acid the product was extracted into dichloromethane. The separated extract was washed with sodium carbonate solution to remove 3-indolylacetic acid and then with water. Evaporation of the solvent gave the crude product as a brown oil. This was distilled at 0.5 – 1 mm pressure (vapour temperature 160° – 190°) and crystallised from toluene (1 l) to give the title compound as white to pale brown crystals m.p. 57° – 59°. Yield 170 g. (70% of theory).

EXAMPLE 2

3-(2-Hydroxyethyl)indole

To a stirred suspension of isopropyl 3-indolylglyoxylate (46.4 g.) in isopropanol (500 ml.), lithium borohydride (13.1 g.) was added in small portions. The resulting solution was heated to reflux and stirred for 5 hours then cooled and diluted with water (2 l.). The mixture was acidified with hydrochloric acid and the product extracted into dichloromethane. The extract was washed with sodium carbonate solution then with water and the solvent was evaporated under reduced pressure to give an oil which was crystallised from toluene (50 ml.). The crude product was a red-brown powder, yield 25.0 g. (78%). This was distilled at 0.5 – 1mm. pressure and the distillate crystallised from toluene (100 ml.), giving 3-(2-hydroxyethyl)indole as white crystals, mp. 57°–59°. Yield 20.7g(64.5%)

EXAMPLE 3

3-(2-Hydroxyethyl)indole

A suspension of benzyl 3-indolylglyoxylate (55.8 g.) and sodium borohydride (22.7 g.) in isopropanol (560 ml.) was heated to reflux over a period of 40 minutes and stirred at that temperature for 4 hours. After cooling the mixture was diluted with water (1.2 l.) and extracted with dichloromethane. The extract was washed with water and the solvent evaporated under reduced pressure to yield a viscous oil. This was distilled at 0.5 – 1 mm. pressure and the friction which distilled at a vapour temperature of 160°–190° was crystallised from toluene (100 ml.), giving the title compound as white crystals, mp. 57°–90°. Yield 24.3 g. (75.5%).

EXAMPLE 4

3-(2-Hydroxyethyl)indole

A stirred suspension of isobutyl 3-indolylglyoxylate (48.5 g.) and sodium borohydride (22.7 g.) in isopropanol (500 ml.) was slowly heated to reflux and held for 5 hours. The cooled mixture was diluted with water (2 l.) and extracted with dichloromethane. The extract was washed with water, dried over magnesium sulphate and concentrated under reduced pressure to an oil which crystallised on cooling. Recrystallisation from toluene (100 ml.) gave 3-(2-hydroxyethyl)indole as a cream-coloured crystalline powder, mp. 55°–56°. Yield 23.3 g. (72.3%).

EXAMPLE 5

3-(2-Hydroxyethyl)indole a. 3-Indolylglyoxylyl chloride (104 g. ) was stirred in diethyl ether (500 ml.) and treated with m-cresol (108 g.) followed by pyridine (79 g.). After stirring for 30 minutes the solid product was collected by filtration, washed with water then with acetonitrile and dried to give m-cresyl 3-indolylglyoxylate as a yellow powder, m.p. 194°–197°. Yield 119 g. (85.5%)

b. A stirred suspension of m-cresyl 3-indolylglyoxylate (55.8 g.) and sodium borohydride (22.7 g.) in isopropanol (300 ml.) was slowly heated to reflux and held for 5 hours. The cooled mixture was diluted with water (2 l.), acidified with hydrochloric acid and extracted with dichloromethane. The extract was washed with sodium carbonate solution, dried and evaporated to give a mobile oil smelling strongly of cresol. This was distilled at 0.5 – 1 mm and the fraction collected at 160°–200° vapour temperature was crystallised from toluene (60 ml.), giving tryptophol as white crystals m.p. 57°–59°.

Yield 17.5 g (54.5%)

EXAMPLE 6

5-Benzyloxy-3-(2-hydroxyethyl)indole

A suspension of methyl 5-benzyloxyindol-3-ylglyoxylate (10 g.) and sodium borohydride (3.7 g.) in isopropanol (100 ml.) was stirred and refluxed for 5 hours. The cooled mixture was diluted with water and extracted with dichloromethane. Evaporation of the extract gave a pale yellow oil which crystallised from a mixture of toluene and petroleum ether to give 5-benzyloxy-3-(2-hydroxyethyl)indole as a white crystalline powder m.p. 97°–98°.

Yield 6.4 g. (74%).

EXAMPLE 7

3-(2-Hydroxyethyl)indole

A suspension of sodium borohydride (22.6 g.) in diglyme (800 ml.) was stirred in a jacketted flask with water cooling. 3-Indolylglyoxylyl chloride (41.5 g.) was cautiously added in small portions then the mixture was heated to 95°–100° for 5 hours. The cooled reaction mixture was diluted with water (2 l.), acidified with hydrochloric acid and extracted with dichloroethane. The extract was washed with sodium carbonate solution then with water and evaporated to give crude tryptophol as a brown oil. This was distilled at 0.1 mm and the distillate collected at 155°–160° was crystallised from toluene (50 ml.), giving pure tryptophol as white crystals m.p. 57°–59°.

Yield: 17.7 g.

EXAMPLE 8

3-(2-Hydroxyethyl)indole

Methyl 3-indolyglyoxylate (30.4g.) was added to a stirred suspension of sodium borohydride (17.0g.) in ethanol (industrial methylated spirit, 300 ml). the exothermic reaction raising the temperature of the mixture from 20° to 45°. After heating to reflux for 5 hours the mixture was cooled, diluted with water (2½ l.) and extracted with dichloromethane. The extract was concentrated under reduced pressure to an oil, which crystallised from toluene (40 ml.) to give the title compound as a buff-coloured powder, purity 98% by GLC.

Yield 15.2g.

EXAMPLE 9

3-(2-Hydroxyl)-2-methylindole a. A solution of 2-methylindole (32.8) in diethyl ether (300 ml.) was added at 30° to oxalyl chloride (35.0g.) diluted with diethyl ether (200 ml.). After stirring for 1 hour the precipitate of 2-methylindolylglyoxylyl chloride was collected by filtration and treated with methanol (300 ml.) to give the methyl ester of 2-methylindol-3-ylglyoxylic acid (30.0 g.) as a red powder m.p. 180°–183°.

b. A stirred suspension of methyl 2-methylindol-3-ylglyoxylate (28 g.) and sodium borohydride (14.5 g.) (300 ml.) was stirred at reflux for 5 hours, then cooled, diluted with water (1.5 l.) and extracted with dichloromethane. After evaporation of the solvent the residual oil was distilled at a pressure of 0.2 mm and the fraction boiling at 140°–160° collected to yield the title compound as a viscous pale yellow oil.

EXAMPLE 10

(a) – (i)

Repeating the procedure of Example 9(a) and (b) the following tryptophols of formula I may be prepared according to the reaction:

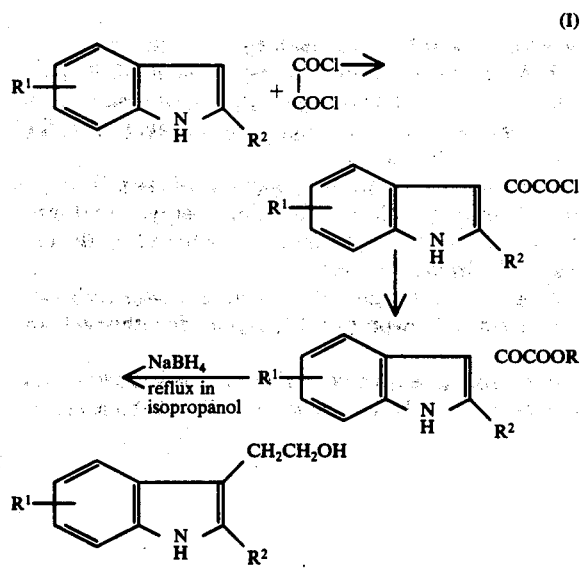

wherein R, $R^1$ and $R^2$ are as defined below:

|     | R | $R^1$ | $R^2$ |
| --- | --- | --- | --- |
| (a) | methyl | 5-methyl | H |
| (b) | ethyl | 6-methyl | H |
| (c) | phenyl | 5-chloro | H |
| (d) | phenethyl | 5-methoxy | H |
| (e) | n-hexyl | 5-ethoxy | H |
| (f) | p-chlorophenyl | 4-bromo | H |
| (g) | methyl | 5-hydroxy | H |
| (h) | methyl | 5-benzyloxy | methyl |
| (i) | p-methylbenzyl | H | H |

I claim:

1. A process for preparing a 1-unsubstituted-3-(2-hydroxyethyl)indole which comprises reducing a 1-unsubstituted-3-indoleglyoxylic acid ester or acid halide with an alkali metal borohydride in the presence of a solvent selected from alkanols of 2 to 6 carbon atoms; ether derivatives of ethylene glycol; and dioxane.

2. A process as claimed in claim 1 in which a 1-unsubstituted-3-indoleglyoxylic acid ester or acid halide of the formula

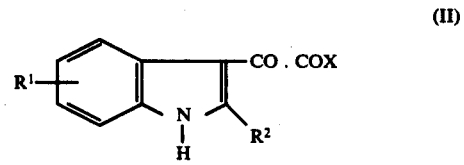

(II)

wherein $R^1$ represents hydrogen, halogen, lower alkyl, lower alkoxy, lower aralkoxy or hydroxy, $R^2$ represents hydrogen, lower alkyl or aryl, and X represents halogen or the group OR wherein R represents alkyl, aryl or aralkyl, is reduced to a 1-unsubstituted-3-(2-hydroxyethyl)indole of formula (I)

-continued

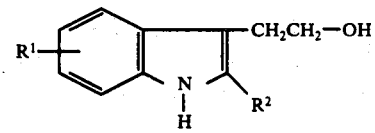

wherein R¹ and R² are as defined hereinabove.

3. A process as claimed in claim 2 wherein R represents lower alkyl; phenyl optionally substituted by halogen, lower alkyl or lower alkoxy; or phenyl lower alkyl to 7 to 12 carbon atoms.

4. A process as claimed in claim 2 wherein R¹ represents hydrogen, chlorine, bromine, methyl, ethyl, propyl, methoxy, ethoxy, benzyloxy, hydroxy, and R² represents hydrogen or methyl.

5. A process as claimed in claim 1 in which the solvent is ethanol, isopropanol, diglyme, dimethoxyethane or dioxane.

6. A process as claimed in claim 1 which is carried out at a temperature between about 78° C and about 180° C.

7. A process as claimed in claim 1 in which the molar ratio of borohydride reducing agent to 1-unsubstituted-3-indoleglyoxylic acid ester or acid chloride is in the range 4:1 to 2:1.

8. A process for preparing tryptophol which comprises reducing a 3-indolyl compound selected from lower alkyl-, phenyl lower alkyl-, phenyl-and lower alkyl phenyl- 3-indolylglyoxylate and 3-indolylglyoxylyl halide using sodium or lithium borohydride in a solvent selected from ethanol, isopropanol or diglyme; the molar ratio of said borohydride to said 3-indolyl compound being in the range 3:1 to 2:1 and the reaction being carried out at a temperature between about 78° C and about 100° C.

9. A process as claimed in claim 8 for preparing tryptophol which comprises the steps of:
  i. reacting indole with oxalyl chloride to give 3-indoleglyoxylyl chloride;
  ii. reacting the 3-indoleglyoxalyl chloride with methanol to give methyl 3-indoleglyoxylate, and
  iii. reducing the methyl 3-indolylglyoxylate using sodium borohydride in refluxing isopropanol.

* * * * *